United States Patent [19]

Gier et al.

[11] Patent Number: 4,806,689

[45] Date of Patent: Feb. 21, 1989

[54] ZEOLITE RHO AS CATALYST FOR CONVERSION OF METHANOL AND AMMONIA TO DIMETHYLAMINE

[75] Inventors: Thurman E. Gier; Robert D. Shannon, both of Chadds Ford, Pa.; George C. Sonnichsen, Wilmington, Del.; David R. Corbin, West Chester, Pa.; Michael Keane, Jr., Wilmington, Del.

[73] Assignee: E. I. Du Pont de Nemours and Company, Wilmington, Del.

[21] Appl. No.: 782,269

[22] Filed: Oct. 3, 1985

Related U.S. Application Data

[63] Continuation-in-part of Ser. No. 672,489, Nov. 16, 1984, abandoned.

[51] Int. Cl.$^4$ .................. C07C 85/02; C07C 85/06
[52] U.S. Cl. ........................ 564/474; 564/479
[58] Field of Search ................... 564/474, 479

[56] References Cited

U.S. PATENT DOCUMENTS

| Re. 19,632 | 7/1935 | Arnold | 260/127 |
|---|---|---|---|
| 1,926,691 | 9/1933 | Swallen et al. | 260/127 |
| 1,992,935 | 3/1935 | Arnold | 260/127 |
| 2,349,222 | 5/1944 | Goshorn | 260/585 |
| 2,394,515 | 2/1946 | Goshorn | 260/583 |
| 2,394,516 | 2/1946 | Goshorn | 260/583 |
| 2,456,599 | 12/1948 | Smith | 260/585 |
| 3,278,598 | 10/1966 | Markiewitz | 260/563 |
| 3,384,667 | 5/1968 | Hamilton | 260/585 |
| 3,387,032 | 6/1968 | Leonard | 260/585 |
| 3,904,738 | 9/1975 | Robson | 423/328 |
| 4,082,805 | 4/1978 | Kaeding | 260/585 |
| 4,191,709 | 3/1980 | Parker et al. | 260/583 |
| 4,254,061 | 3/1981 | Weigert | 564/479 |
| 4,313,003 | 1/1982 | Weigert | 564/463 |
| 4,398,041 | 8/1983 | Cochran et al. | 564/479 |
| 4,434,300 | 2/1984 | Deeba et al. | 564/479 |
| 4,436,938 | 3/1984 | Tompsett | 564/474 |
| 4,485,261 | 11/1984 | Ashina et al. | 564/479 |
| 4,683,334 | 7/1987 | Bergna et al. | 564/474 |

FOREIGN PATENT DOCUMENTS

| 0085408 | 10/1983 | European Pat. Off. |
| 56-53887 | 4/1981 | Japan . |
| 422563 | 7/1933 | United Kingdom . |

OTHER PUBLICATIONS

Chen et al., "Industrial Application of Shape-Selective Catalysis", *Catal. Rev.-Sci. Eng.*, 28(2&3), 185-264 (1986).

Restelli et al., *A. I. Ch. E. Journal* 12:292 (1966).

Mochida et al., Journal of Catalysis 82:313 (1983).

Robson et al., "Synthesis and Crystal Structure of Zeolite Rho—A New Zeolite Related to Linde Type A", Advances in Chemistry Series 121, (American Chemical Society 1973).

*Primary Examiner*—Glennon H. Hollrah
*Assistant Examiner*—John A. Sopp

[57] ABSTRACT

A process is provided for producing dimethylamine, comprising reacting methanol and/or dimethylether and ammonia, in amounts sufficient to provide a carbon/nitrogen (C/N) ratio of from about 0.2 to about 1.5, at a temperature from about 250° C. to about 450° C., in the presence of a catalytic amount of an acidic zeolite rho.

26 Claims, No Drawings

ZEOLITE RHO AS CATALYST FOR CONVERSION OF METHANOL AND AMMONIA TO DIMETHYLAMINE

CROSS-REFERENCE TO RELATED APPLICATION

The present application is a continuation-in-part application of U.S. patent application Ser. No. 672,489 filed Nov. 16, 1984, now abandoned.

BACKGROUND OF THE INVENTION

This invention involves a process for making amines, particularly dimethylamine, in which methanol and/or dimethylether and ammonia are contacted in the presence of a selected zeolite catalyst.

Methylamines are generally prepared in industrial quantities by continuous reaction of methanol and ammonia in the presence of a silica-alumina catalyst. The reactants are typically combined in the vapor phase, at temperatures in the range of 300° to 500° C., and at elevated pressures. Trimethylamine is the principal component of the resulting product stream, accompanied by lesser amounts of monomethylamine and dimethylamine. From a commercial standpoint, the most valued product of the reaction is dimethylamine, in view of its widespread industrial use as a chemical intermediate. Accordingly, a major objective of those seeking to enhance the commercial efficiency of this process has been to improve overall yields of dimethylamine, and to a lesser extent, monomethylamine, relative to trimethylamine. Among the approaches taken to meet this objective are recycling of trimethylamine, adjustment of the ratio of methanol to ammonia reactants, and use of selected dehydrating or aminating catalyst species. Due to the commercial importance of the process, a rather extensive compendium of patents and other contributions to the technical literature has resulted. Representative references generally relevant to the field of the present invention are summarized in the following paragraphs.

Swallen, U.S. Pat. No. 1,926,691, discloses a process for producing dimethylamine by disproportionating monomethylamine over dehydrating or aminating catalysts such as alumina, silica, thoria, aluminum silicate or partially dehydrated aluminum trihydrate.

Arnold, U.S. Pat. No. 1,992,935, describes a process for catalytic synthesis of amines from alcohols and ammonia which employs as catalyst a dehydrating oxide, e.g., alumina, deposited on the surface of a porous, rigid gel, e.g., silica gel.

Arnold, U.S. Pat. No. Re. 19,632, discloses a process improvement in which trimethylamine is introduced with the methanol and ammonia reactants to shift reaction equilibrium in favor of dimethylamine production.

Johnson, British Pat. No. 422,563, discloses a process for producing aliphatic amines involving heating an alcohol or ether under a pressure of more than about 50 atmospheres in the presence of a "catalyst capable of splitting off water" (e.g., alumina), with an excess of ammonia and optionally with addition of primary amine to the reaction mixture.

Goshorn, U.S. Pat. No. 2,349,222, discloses use of granular alumina coated with one or more oxides of nickel, cobalt, or chromium as a catalyst for alkylation of ammonia to produce alkyl amines. Goshorn, U.S. Pat. Nos. 2,394,515 and 2,394,516, discloses use as catalyst of an aluminum salt or oxide coated with silica and vanadium or molybdenum oxide.

Smith, U.S. Pat. No. 2,456,599, discloses a process improvement wherein water is added to a reactant feed mixture of methanol and ammonia to repress formation of tertiary amine in favor of primary and secondary amine.

Markiewitz, U.S. Pat. No. 3,278,598, discloses use of a rhodium, palladium, or ruthenium cocatalyst in conjunction with Raney metals to increase production of secondary amines from the reaction of alcohols and ammonia.

Rostelli et al., *A. I. Ch. E. Journal* 12: 292 (1966) describe studies of transmethylation reactions of monomethylamine and dimethylamine over montmorillonite, a hydrated magnesium or calcium oxidecontaining aluminosilicate having a porous lattice structure. For transmethylation of monomethylamine, this work indicated that reaction rate was directly proportional to reactant partial pressure, indicating that the rate-determining event is adsorption of reactant to the catalyst surface.

Hamilton, U.S. Pat. No. 3,384,667, describes alkylation of ammonia in the presence of a dehydrated crystalline aliminosilicate catalyst having pores of a diameter permitting absorption of primary and secondary, but not tertiary, amine products.

Leonard, U.S. Pat. No. 3,387,032, discloses a process for reacting ammonia with methanol and/or dimethyl ether in the presence of a catalyst consisting of a silica gel base impregnated with 10–15% alumina which is first steam-deactivated and then treated with silver, rhenium, molybdenum, or cobalt ions to promote selectivity for dimethylamine.

Kaeding, U.S. Pat. No. 4,082,805, discloses use of a crystalline aluminosilicate or zeolite catalyst having the structure of ZSM-5, ZSM-11 or ZSM-21 in a process for producing amines by reaction of ammonia with $C_1$–$C_5$ alcohols at elevated temperatures and pressures.

Parker et al., U.S. Pat. No. 4,191,709, describe use of a hydrogen form of zeolite FU-1 or zeolite FU-1 in which some or all of the protons have been replaced by bivalent or trivalent cations.

Weigert, U.S. Pat. No. 4,254,061, discloses a process in which production of monomethylamine is enhanced by reacting methanol and ammonia in amounts sufficient to provide a C/N ratio of 0.5 to 1.5 over a catalyst selected from (a) mordenite wherein the primary cation is Li, Na, HNa having at least 2% Na by weight, K, Ca, Sr, Ba, Ce, Zn or Cr;

(b) ferrierite wherein the primary metal cation is Li, Na, K, Ca, Sr, Ba, Ce or Fe;

(c) erionite ore;

(d) calcium erionite, and (e) clinoptilolite ore;

at a temperature of 250°–475° C. and a pressure of 7–7000 kPa, a contact time, normalized to 7 kPa, of 0.1 to 60 seconds, and a methanol conversion of 15–95%.

Ashina et al., Japanese published patent application No. 56-53887, and Mochida et al., *Journal of Catalysis* 82: 313 (1981), also disclose use of mordenite zeolites to enhance production of dimethylamine in closely related variants of the process disclosed by Weigert.

Weigert, U.S. Pat. No. 4,313,003, discloses an improved process for disproportionating monomethylamine to dimethylamine and ammonia, comprising passing monomethylamine over a crystalline aluminosilicate catalyst selected from (a) mordenite wherein the primary cation is Na, HNa having at least 2% Na, Mg, Ca, Sr or Ba;

(b) ferrierite wherein the primary metal cation is Na, K, Mg, Ca, Sr or Ba;

(c) clinoptilolite and (d) phillipsite;

at a temperature of 250°–475° C. and a pressure of 7–7000 kPa, at a feed rate of 0.1–10 grams of monomethylamine per gram of catalyst per hour, at a monomethylamine conversion of 15–75%.

Cochran et al., U.S. Pat. No. 4,398,041, describe a process for converting $C_1$–$C_4$ alcohols to a non-equilibrium controlled distribution of primary, secondary, and tertiary alkylamines. The process disclosed involves passing a mixture of reactant alcohols and ammonia into a first conversion zone containing a "shape-selective" crystalline aluminosilicate catalyst having a pore size selective for mono and disubstituted alkylamine products; dividing the resulting product stream; passing one portion of this product stream to a second conversion zone containing another catalyst having a different pore size distribution; and combining the remaining portion of the first product stream with the product stream of the second conversion zone to yield a non-equilibrium controlled product distribution. The zeolite catalysts disclosed by this reference include 5A zeolite, REY zeolite, H-chabazite-erionite, H-erionite, H-mordenite, and H-Y zeolite.

Deeba et al., published European patent application No. 0085408, disclose a method for improving methanol conversion rates comprising reacting methanol and ammonia over a highly acidic dehydrated aluminosilicate catalyst having a silicon to aluminum ratio of at least 2.0 and manifesting microporous diffusivity for methylamines.

Deeba et al., U.S. Pat. No. 4,434,300 disclose a method for improving methanol conversion rates in the reaction of methanol and ammonia to produce methylamines which comprises effecting the reaction in the presence of a macroporous, highly acidic aluminosilicate.

Tompsett, U.S. Pat. No. 4,436,938, discloses a process for making methylamines comprising reacting methanol and/or dimethyl ether over a binderless zeolite A catalyst, preferably a binderless zeolite 5A catalyst.

Currently, methylamines are produced using an adiabatic plug flow reactor. Although specific conditions do vary depending upon ammonia feed ratio and amount of product recycle, reactor inlet temperatures are generally maintained from about 310° C. to 340° C., and outlet temperatures generally run from about 400° C. to about 430° C. The difference between inlet and outlet temperatures is due to exothermicity of the reaction and is moderated by recycling of ammonia and trimethylamine. The foregoing temperatures represent a compromise between increasing production rates at a given reactor size, which is favored at higher reaction temperatures, and reducing catalyst deactivation, which is minimized at lower reaction temperatures. More active catalysts permit operation at lower reaction temperatures, increasing catalyst lifetime and/or decreasing the need to recycle ammonia or trimethylamine.

As the foregoing discussion suggests, new process improvements which optimize dimethylamine yields and suppress production of trimethylamine and which allow lower reaction temperatures while maintaining reactor throughput in this widely-practiced process are of significant interest to the chemical industry.

SUMMARY OF THE INVENTION

The present invention provides a process for producing dimethylamine comprising reacting methanol and/or dimethylether and ammonia, in amounts sufficient to provide a carbon/nitrogen (C/N) ratio from about 0.2 to about 1.5, at a temperature from about 250° C. to about 450° C., in the presence of a catalytic amount of an acidic zeolite rho.

DETAILED DESCRIPTION OF THE INVENTION

Zeolites can be generically described as complex aluminosilicates characterized by a three-dimensional framework structure enclosing cavities occupied by ions and water molecules, all of which can move with significant freedom within the zeolite matrix. In commercially useful zeolites, the water molecules can be removed from or replaced within the framework without destroying its geometry. Zeolites can be represented by the following formula:

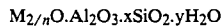

$$M_{2/n}O.Al_2O_3.xSiO_2.yH_2O$$

wherein M is a cation of valence n, $x \geq 2$, and y is a number determined by the porosity and the hydration state of the zeolite, generally from 2 to 8. In naturally-occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

Zeolite structure consists of corner-linked tetrahedra with Al or Si atoms at centers of tetrahedra and oxygen atoms at corners. Such tetrahedra are combined in a well-defined repeating structure comprising various combinations of 4-, 6-, 8-, 10-, and 12-membered rings. The resulting framework consists of regular channels and cages, which impart a useful pore structure for catalysis. Pore dimensions are determined by the geometry of the aluminosilicate tetrahedra forming the zeolite channels or cages, with nominal openings of 2.6 Angstroms for 6-rings, 4.0 Angstroms for 8-rings, and 5.5 Angstroms for 10-rings. Pore dimensions are critical to catalytic performance, since this characteristic determines whether reactant molecules can enter and product molecules can exit the zeolite framework. In practice, it has been observed that very slight decreases in ring dimensions can effectively hinder or block movement of particular reactants or products within a zeolite structure.

The pore dimensions which control access to the interior of the zeolite are determined not only by the tetrahedra forming the pore opening, but also by the presence or absence of ions in or near the pore. In the case of zeolite A, for example, access can be restricted by monovalent ions, such as $Na^+$ or $K^+$, which are situated in or near 8-ring openings as well as 6-ring openings. Access is enhanced by divalent ions, such as $Ca^{2+}$, which are situated only in or near 6-rings. Thus KA and NaA exhibit effective pore openings of about 0.3 nm and 0.4 nm respectively, whereas CaA has an effective pore opening of 0.5 nm.

Useful references generally relating to zeolite structure and characterization include the following:

Meier et al., *Atlas of Zeolite Structure Types* (International Zeolite Assn. 1978); Mumpton, "Natural Zeolites" in *Reviews in Mineralogy* 14: 1 (1977); Smith, "Origin and Structure of Zeolites" in *Zeolite Chemistry and Catalysis*, ACS Monograph 171 (American Chemical Society, 1976).

General Characteristics of Zeolite Rho

Zeolite rho, the zeolite species employed in the process of the present invention, is a small-pore synthetic zeolite which can be described by the formula $$(Na,Cs)_{12}Al_{12}Si_{36}O_{96}\cdot 44H_2O.$$

The structure and synthesis of this synthetic zeolite are described by Robson et al., "Synthesis and Crystal Structure of Zeolite Rho—A new Zeolite Related to Linde Type A", *Advances in Chemistry Series* 121 (American Chemical Society 1973), and Robson, U.S. Pat. No. 3,904,738. The combined disclosures of these references are incorporated by reference herein.

The cationic species $Na^+$ and $Cs^+$ present in rho zeolites can be exchanged for protons in a conventional ion exchange with $H^+$ or by conversion to an ammoniated form ($NH_4$-rho) which is subsequently converted to the acid form by calcination at elevated temperatures.

Acid forms of zeolites can be prepared by a variety of techniques including ammonium exchange followed by calcination, direct exchange of alkali ions for protons using mineral acids or ion exchangers, and by introduction of polyvalent ions (for a discussion of acid sites in zeolites, see J. Dwyer, "Zeolite Structure, Composition and Catalysis" in *Chemistry and Industry*, Apr. 2, 1984). The acid sites produced are generally believed to be of the Bronsted (proton donating) type or of the Lewis (electron pair accepting) type. Bronsted sites are generally produced by deammoniation at low temperatures, exchange with protons, or hydrolysis of polyvalent cations. Lewis sites are believed to arise from dehydroxylation of the H-zeolites or from the presence of polyvalent ions. In the acidic zeolite catalysts of the present invention, Bronsted and/or Lewis sites can be present.

The crystal structure of zeolite rho is characterized by large cuboctahedral cages linked by double 8-rings, defining pore openings of approximately 3.9 Angstroms by 5.1 Angstroms (0.39×0.51 nm). One unusual characteristic of the structure of zeolite rho is the presence of two independent 3-dimensionally-connected systems of channels. A further unique structural feature, described by Parise et al., *J. Phys. Chem.* 88: 1635 (1984) is a structural change occurring upon dehydration which results in an increase in ellipticity of the aforementioned 8-ring pore openings. If a dehydrated sample of zeolite rho is heated further, an increase in unit cell dimensions results, accompanied by a decrease in ellipticity of the 8-ring pore openings.

It should be noted that catalytic selectivity for dimethylamine provided by zeolite rho cannot be attributed solely to its geometry. Other factors, for example, the number and nature of acid sites on internal and external surfaces, crystallite size, external surface modifiers, and contaminants can also be expected to affect selectivity for dimethylamine.

For example, introduction of alkali metal or alkaline earth metal cations into the structure of zeolite rho by ion exchange can alter the effective size of channels and thus facilitate or hinder passage of reactant or product molecules during a reaction. Thus, cation exchange can be employed as a means of enhancing selectivity of zeolite rho for dimethylamine.

A criterion based upon empirical observations of zeolite sorption characteristics has been devised in order to assess the utility of various small-pore zeolites as catalysts for conversion of methanol and ammonia to dimethylamine. This criterion, which is herein denominated the geometric selectivity index for dimethylamine, or GSI, is defined as net sorption of methanol (MeOH) divided by net sorption of n-propanol (n-PrOH), each measured at 25° C. following 20 hours' exposure to sorbate vapor. Sorption is expressed in weight percent (grams sorbate per 100 grams zeolite).

Sorption measurements are made using an apparatus substantially analogous to that described by Landolt, *Anal. Chem.* 43: 613 (1971). In a typical experiment, 0.4 to 1 g of zeolite is pressed at 300–1000 psi into a self-supporting cylinder, inserted into a pre-weighed sample holder, evacuated, heated to 425° C., cooled, and then weighed in the sample holder. The resulting sample is then exposed to sorbate vapor at 10–50% of its vapor pressure at 25° C. in a sorption manifold, removed from the sorption manifold, and weighed again to determine sorption.

Small-pore zeolites other than zeolite H-rho demonstrate increased selectivity for dimethylamine with increased GSI. Surprisingly, however, zeolite H-rho does not show such a correlation. GSI observed for zeolite H-rho samples remains nearly constant with significant increases in selectivity.

Catalyst Preparation

Zeolite rho is synthesized in a Na-Cs form substantially according to the procedure of Robson, U.S. Pat. No. 3,904,738. In one method of preparing the H-form employed in the process of this invention, $Na^+$ and $Cs^+$ ions are exchanged for $NH_4^+$ ions and the resulting $NH_4^+$ form is deammoniated by calcination at 400° C. to 800° C. Although ion exchange of ammonium for $Na^+$ and $Cs^+$ ions may be incomplete in any given experiment, typically leaving 0.5–1.0 Cs per unit cell, the product of ion-exchange is referred to herein as $NH_4$-rho. Similarly, although deammoniation of $NH_4$-rho may not result in complete conversion of all $NH_4^+$ to $H^+$ or other acid sites, particularly when a sample is calcined at lower temperatures, the resulting product is referred to herein as "zeolite H-rho".

A form of zeolite H-rho containing very low levels of residual $Cs^+$ ion can be generated by treating zeolite H-rho with NaOH solutions followed by exchange with $NH_4^+$-ion containing solutions and calcination. Repetition of these steps provides a form of zeolite H-rho with particularly enhanced selectivity for dimethylamine.

Identification of zeolite Na, Cs-rho is generally made by X-ray powder diffraction. The integrated intensities of the observed X-ray peaks can be used as a measure of zeolite crystallinity. High intensities indicate a highly crystalline product, while low intensities indicate a less crystalline material. However, as crystallite size falls below about 50 nm, X-ray diffraction peaks broaden (H. P. Klug and L. E. Alexander, *X-Ray Diffraction Techniques*, Wiley-Interscience, N. Y., 1974). When crystallite size falls below about 2–6 nm, peaks become so broad that they are difficult to detect by conventional analog recording spectrometers.

However, despite a lack of measurable X-ray peak intensity, such "X-ray amorphous" zeolite crystallites are capable of shape selective catalysis, as recently reported by Jacobs et al., *J. Chemical Society, Chemical Communications*, p. 591 (1981). For such crystallites, zeolite crystallinity is evident from infra-red spectra, sorption measurements, and catalytic shape selectivity. The acidic rho zeolites of the present invention can be highly crystalline, poorly crystalline, or X-ray amorphous crystallites.

Cation-exchanged forms of zeolite rho can be prepared from a Na, Cs form zeolite rho or from zeolite H-rho by contacting a crystalline form of the zeolite with a solution containing the ion to be exchanged. Repeated applications of fresh solutions are necessary to obtain a significant degree of cation exchange. As used throughout the specification, the term "zeolite Ca-rho" or "Ca-rho" refers to a cation-exchanged form of zeolite rho wherein the cation is Ca.

It is known (Robson, U.S. Pat. No. 3,904,738; Barrer et al., *Proc. 5th Conf. on Zeolites*, Naples, 1980, pp. 20–29) that small amounts of chabazite and pollucite impurities are frequently found in rho preparations. It is believed that these impurities and small quantities of residual gel are not selective to dimethylamine, and thus might reduce the selectivity to a degree dependent upon the quantity present in individual samples.

It has previously been established (Kerr, "Hydrogen Zeolite Y, Ultrastable Zeolite Y, and Aluminum-Deficient Zeolites", in *Molecular Series, Advances in Chemistry Series* 121: 210 (American Chemical Society 1973)) that $NH_4$-zeolites deammoniated by deep-bed calcination techniques exhibit properties distinct from those of zeolites deammoniated by shallow-bed calcination techniques. Deep-bed calcination refers to combinations of bed geometry and calcination conditions, e.g., thick beds and/or slow flow of gas over zeolite, which do not result in rapid removal of gaseous $H_2O$ and $NH_3$ from the heated zeolite. In contrast, shallow-bed calcination refers to bed geometries and conditions, e.g., shallow beds and rapid stripping of gases from the bed, which maximize removal of $H_2O$ and $NH_3$ from zeolite.

The nature of the differences between acid forms of zeolite rho as prepared by the above described techniques has not been precisely pinpointed. It has been suggested, however, that products of deep-bed calcination conditions contain nonframework Al species which have dissociated from the zeolite lattice during the deammoniation process. Freude et al., *Zeolites* 3: 171 (1983) have shown that, according to temperature and the degree of deep-bed calcination of zeolite $NH_4$—Y, nonframework Al species containing octahedrally-coordinated Al are progressively condensed. Presumably such nonframework species function as catalytically active sites or as modifiers of other catalytically active sites. Conceivably, such highly-condensed species present following high temperature calcination are responsible for the surprisingly high proportion of dimethylether produced over zeolite H-rho calcined at high temperatures under deep-bed conditions. Alternatively, the high dimethylether yields might be caused by other catalytic sites produced during the dealumination process and the extra lattice Al phase might not be directly involved. As illustrated by the Examples set forth below, the method of deammoniation significantly affects catalytic activity, and hence, product distribution, when acid forms of zeolite rho are employed as catalysts in the reaction of methanol and ammonia to produce mono-, di-, and trimethylamine.

Clearly, a continuous gradation of calcination conditions can be arranged between extreme "deep-bed" conditions and extreme "shallow-bed" conditions. Accordingly, definitions regarding such conditions are by necessity somewhat arbitrary, and various equivalents to the conditions for calcination set forth below can be arranged. However, the definitions for calcination conditions set forth in Table I, below, apply throughout the specification.

TABLE I

| | Catalyst Calcination Conditions | | |
|---|---|---|---|
| | Bed Type | | |
| | Shallow-Bed | Quasi-Deep-Bed | Deep-Bed |
| Bed Thickness (mm) | ≦3 | >3 | >3 |
| Gas Flow Conditions | Rapid or continuous gas flow, vacuum gas removal, or fluidized bed conditions maintained during calcination | Same as shallow-bed calcination | Little or no gas flow during calcination |
| Temperature (°C.) | 400–750 | 400–800 | 500–650 (preferred; reduced DME production) |
| | 600–750 (preferred) | | 650–800 (greater DME production) |

In general, zeolite H-rho exhibits greater selectivity to dimethylamine when the $NH_4$-form is calcined at higher temperatures and/or for longer times. Increased deammoniation temperatures appear to be more effective than increased calcination periods for increasing selectivity to dimethylamine. However, deep-bed calcinations at high temperatures (>650° C.) can result in a catalyst with higher levels of dimethylether (DME) production than those at lower temperatures. Use of catalysts prepared under shallow-bed conditions generally results in lower levels of DME production.

Generally, calcination temperatures must be sufficiently high to convert substantially all $NH_4^+$ sites to $H^+$ sites and other acid sites, yet not high enough to render significant amounts of the zeolite amorphous. The presence of $NH_4^+$ in a given sample can be determined by infrared measurements. Excessive calcination can lead to collapse of zeolite crystalline structure and an amorphous state, which is to be distinguished from the "X-ray amorphous" zeolitic materials described above. The "X-ray amorphous" zeolites are obtained by limiting crystallization times, so that very small zeolite crystallites result. These crystallites exhibit characteristic zeolite selectivity, but permit rapid ingress of reactant molecules and egress of product molecules due to their small size.

Where deep-bed conditions are employed and DME production is undesirable, calcination temperatures of about 500° to 650° C. are preferred. If DME production can be tolerated, the upper limit for calcination temperature can be extended to about 800° C. Under shallow-bed conditions, calcination temperatures of about 400° to 750° C. can be employed. Temperatures of 600°–750° C. are preferred.

Dimethylamine selectivity and catalyst activity depend on the degree of hydration of zeolite rho. Both selectivity and activity are significantly higher with a hydrated zeolite rho catalyst than with a dehydrated zeolite rho catalyst. It is therefore preferred to use a zeolite rho in a hydrated state.

The degree of hydration depends on the calcination conditions and the conditions to which the zeolite is exposed following calcination, i.e., the temperature, the relative humidity of the atmosphere, and the length of time between zeolite calcination and use as a catalyst. The degree of hydration can be described by a zeolite adsorption isotherm as illustrated by Breck, *Zeolite Molecular Sieves*, (John Wiley & Sons, New York, 1960) p. 600. At 20° C. and typical $H_2O$ partial pressures of 5–20 mm Hg, most zeolites contain a significant amount of water of hydration. The time dependence of the degree of hydration of zeolite rho under ambient conditions is not well-documented in the literature but rehydration measurements on zeolite H-rho show that a degree of hydration of 70–80% is reached in 3–5 days and the maximum degree of hydration is reached after a period of months.

Process Conditions

As previously noted, the process of the present invention comprises reacting methanol and/or dimethylether (DME) and ammonia, in amounts sufficient to provide a carbon/nitrogen (C/N) ratio from about 0.2 to about 1.5, at a temperature from about 250° C. to about 450° C., in the presence of a catalytic amount of an acidic zeolite rho, of which zeolites H-rho and Ca-rho are examples. Reaction pressures can be varied from 1–1000 psi (7–7000 kPa) with a methanol/DME space time of 0.01 to 80 hours. The resulting conversion of methanol and/or DME to methylamines is generally in excess of 85% (on a mole basis) and selectivity (on a mole basis) to dimethylamine is generally greater than 40%. In addition, selectivity to and yield of trimethylamine is suppressed. Thus, molar yields of dimethylamine generally exceed 40% and molar yields of trimethylamine generally are less than 30% under the process conditions of the present invention.

The process variables to be monitored in practicing the process of the present invention include C/N ratio, temperature, pressure, and methanol/DME space time. The latter variable is calculated as catalyst mass divided by the mass flow rate of methanol and DME introduced to a process reactor, (mass catalyst/mass methanol+DME fed per hour).

Generally, if process temperatures are too low, reduced conversion of reactants to dimethylamine will result. On the other hand, if temperatures are excessively high, equilibrium conversions and catalyst deactivation can occur. Preferably, temperatures are maintained between about 300° C. and about 400° C., with lower temperature within this range especially preferred in order to minimize catalyst deactivation. At relatively low pressures, products must be refrigerated to condense themm for further purification, adding cost to the overall process. However, excessively high pressures require costly thick-walled reaction vessels. Preferred pressures range from 10–500 psi (70–3000 kPa). Short methanol/DME space times result in low conversions and tend to favor the production of monomethylamine. Long methanol/DME space times may result either in inefficient use of catalyst or production of an equilibrium distribution of methylamines at very high conversions. Generally, methanol/DME space times of 0.01–80 hours are satisfactory, with methanol/DME space times of 0.10–1.5 hours being preferred (corresponding to methanol/DME space velocities of 0.013–100 g methanol+DME/g catalyst/hour, preferably 0.67–10 g methanol+DME/g catalyst/hour).

The reactant ratio of methanol and/or DME to ammonia, herein expressed as the C/N ratio (g atoms C/g atoms N), is critical to the process of the present invention. As the C/N ratio is decreased, production of monomethylamine is increased. As the C/N ratio is increased, production of trimethylamine increases. Catalyst deactivation is also greater at high C/N ratios. Accordingly, for best results, C/N ratios should be maintained between 0.2 to 1.5, and preferably from 0.5 to 1.2 in conducting the process of the present invention.

The efficiency of the process of the invention is measured by overall conversion of methanol and/or DME to methylamines, and by selectivity of dimethylamine production. For example, if methanol is used as the sole reactant, overall conversion is determined by comparison of the amount (in moles) of methanol in the product mixture, which is considered to be unconverted, to the amount in the reactant feed. Thus, overall conversion, in percent, is given by:

$$100\left(1 - \frac{\text{Moles MeOH in product}}{\text{Moles MeOH in feed}}\right)$$

Conversion of methanol to methylamines, in percent, is given by:

$$100\left(1 - \frac{\text{Moles MeOH in product} + 2(\text{Moles DME in Product})}{\text{Moles MeOH in feed}}\right)$$

Conversion of methanol to monomethylamine (MMA) in percent, is given by:

$$100\left(\frac{\text{Moles MMA}}{\text{Moles MeOH in feed}}\right)$$

Similarly, conversion of methanol to dimethylamine (DMA), in percent, is given by:

$$100\left(\frac{2(\text{Moles DMA})}{\text{Moles MeOH in feed}}\right)$$

and conversion of methanol to trimethylamine (TMA), in percent, is given by:

$$100\left(\frac{3(\text{Moles TMA})}{\text{Moles MeOH in feed}}\right)$$

Finally, selectivity to DMA is calculated by analysis of product composition. Thus, selectivity to DMA, in percent, is provided by the following expression:

$$100\left(\frac{2[\text{DMA}]}{[\text{MMA}] + 2[\text{DMA}] + 3[\text{TMA}]}\right)$$

For efficient operation, the catalyst must be selective at high conversion (87–98%) and a C/N ratio of 0.5–1.2.

In practicing the process of the invention, the zeolite catalyst can be combined with another material resistant to the temperature and other conditions employed in the process. Such matrix materials include synthetic or natural substances such as clays, silica, and metal oxides.

Comparison of selectivities for different samples should be made at similar conversions, since selectivity changes with conversion. At low conversions, MMA production is favored; at very high conversion, the reaction will approach an equilibrium distribution and thus result in increased TMA production.

The process of the present invention can be further understood by reference to the following Examples, wherein all temperatures are expressed in degrees Celsius (°C.) and all percentages are by weight unless otherwise indicated. In composition determinations, it was assumed that there were 96 oxygen atoms per unit cell. Analysis determined the relative amounts of the various cations present, and remaining positively-charged species were assumed to be hydrogen.

EXAMPLE 1

A sample of zeolite H-rho, which was employed as catalyst in this Example and Example 2, below, was prepared as follows. A mixture having the composition $2.80Na_2O.0.5Cs_2O.Al_2O_3.11.1SiO_2.120H_2O$ was formed by adding 90 mL 4M $Na_2AlO_2OH$, 31.5 mL 5.79N CsOH, and 13 g NaOH to 355 mL colloidal silica (Ludox® LS-30) in a polypropylene container. The resulting mixture was allowed to stand at 25° for 9 days, and then heated at 100° for 10 days. The resulting product was washed several times and then allowed to stand in contact with a 23% $NH_4NO_3$ solution for about 65 hours to produce $NH_4$-rho. This material was then converted to H-rho by calcination at 415° in air for about 16 hours under deep-bed conditions. Analysis of the resulting sample of zeolite H-rho indicated its composition to be $Cs_{0.74}Na_{0.2}H_{10.22}Al_{11.16}Si_{36.84}O_{96}$.

The zeolite H-rho was then molded into 1 inch (2.54 cm) diameter pellets under 20,000 psi. The pellets were crushed and sieved to a −20/+40 ASTM Std. Sieve No. (425 μm-850 μm) powder.

Two grams of this sieved powder of zeolite H-rho were placed in a stainless-steel U-tube reactor 0.125 in (0.55 cm) in diameter and about 12 in (30 cm) in length. The reactor was placed in a fluidized sand bath and heating of the reactor to reaction temperature was begun. To insure that the reactants were in the vapor state when they contacted the catalyst, the reactor was allowed to reach a temperature of about 200° C. before reactant flow was started. The time to heat the reactor from ambient temperature to about 200° C. was about ½ hour.

This experiment and that reported in Example 2, below were conducted at atmospheric pressure (14.7 lbs-in$^{-2}$, 101 kPa). Reactants methanol and ammonia were fed to a preheater as a liquid mixture at a molar ratio of about 1, vaporized, and then passed through the reactor into contact with the catalyst. Reaction temperatures and reactant flow rates are shown in Table II, below.

The reactor effluent was analyzed by gas chromatography for ammonia, dimethylether (DME), methanol, water, and mono-, di-, and trimethylamine. The percentage conversions of methanol (overall), of methanol to methylamines (MA), and the percentage selectivities of conversion to each methylamine species are given in Table II, below. That portion of methanol converted to other than methylamines was converted to DME in this and all other Examples reported herein.

EXAMPLE 2

A portion of the zeolite H-rho preparation described in Example 1, above, was heated in flowing $N_2$ at 500° for 2 hrs under quasi-bed calcination conditions. 2 g of this material were placed in a reactor and employed in a catalyst evaluation experiment conducted substantially similarly to that reported in Example 1. The results of this experiment are set forth in Table II, below:

TABLE II
Use of Zeolite H—rho as Catalyst for Dimethylamine Synthesis

| Example | Calcination T (°C.) | Calcination Time (hr) | Reactor T (°C.) | MeOH Feed Flow (mL/hr) | MeOH Conv. (%) | MeOH—MA Conv. (%) | Selectivity (%) MMA | DMA | TMA |
|---|---|---|---|---|---|---|---|---|---|
| 1 | 415 | 16 | 350 | 12 | 85 | 79 | 16 | 36 | 48 |
| 2 | 500 | 2 | 300 | 3 | 87 | 84 | 19 | 48 | 33 |

EXAMPLES 3-11

The results of Examples 3 through 11, which are set forth in Table III, below, illustrate the relationship between selectivity to methylamine products and feed flow rate and pressure. DMA yields in excess of 40% at a C/N ratio of 1 were obtained in each of Examples 3-11. The zeolite H-rho employed as catalyst in these examples were prepared by the following procedure:

A mixture of 200 mL 4M $Na_2AlO_2OH$, 56 mL 50% CsOH, and 26 g NaOH was added to 720 mL of colloidal silica (Ludox® LS-30) in a polytetrafluoroethylene (Teflon®) bottle, and permitted to stand at 25° for 9 days. The resulting mixture was then heated at 100° for 7 days, allowed to stand at 25° for an additional 3 days, and then reheated to 100° for 24 hrs. The resulting product was then washed and contacted overnight 3 times with a 20% $NH_4NO_3$ solution. The resulting preparation of zeolite $NH_4$-rho indicated a formula upon analysis of

$(NH_4)_{9.6}Cs_{1.1}Al_{10.3}Si_{37.7}O_{96}.42.9H_2O$.

A portion of this material was converted to H-rho by calcination at 550° in air for 18 hrs under deep-bed conditions.

The catalyst evaluation experiments of Examples 3-11, which are reported in Table III, were conducted substantially similarly to Example 1, above. Examples 3-11 demonstrate the higher flows and lower methanol conversions increase selectivity to MMA and decrease selectivity to TMA. In addition, Examples 3-11 indicate that increased reactor pressure increases selectivity to DMA and decreases selectivity to TMA when compared at similar methanol conversions.

TABLE III

Effect of Feed Flow Rate and
Pressure on H—rho Selectivity for Dimethylamine

| Example | Pressure (PSIA/kPa) | T (°C.) | Feed Flow (mL/hr) | MeOH Conv. (%) | MeOH—MA Conv. (%) | Selectivity (%) MMA | DMA | TMA |
|---|---|---|---|---|---|---|---|---|
| 3 | 14.7/101 | 300 | 16 | 67 | 65 | 31 | 57 | 13 |
| 4 | 14.7/101 | 300 | 12 | 80 | 78 | 23 | 60 | 16 |
| 5 | 14.7/101 | 300 | 8 | 86 | 84 | 21 | 60 | 20 |
| 6 | 14.7/101 | 300 | 6 | 92 | 90 | 18 | 60 | 22 |
| 7 | 14.7/101 | 300 | 4 | 98 | 96 | 16 | 59 | 25 |
| 8 | 120/830 | 300 | 48 | 66 | 65 | 29 | 63 | 7 |
| 9 | 120/830 | 300 | 32 | 86 | 85 | 19 | 68 | 12 |
| 10 | 120/830 | 300 | 16 | 92 | 91 | 18 | 70 | 12 |
| 11 | 120/830 | 300 | 8 | 98 | 97 | 15 | 63 | 22 |

EXAMPLES 12-19

Examples 12-19 illustrate the effects of high deep-bed calcination temperatures and extended calcination times upon selectivity to DMA for H-rho zeolites. In general, increasing calcination temperatures and lengthening calcination times increase selectivity to DMA, but also increase conversion of methanol to dimethylether (DME).

Each sample of zeolite H-rho evaluated in Examples 12-15 was evaluated for sorption of methanol and n-propanol. The following procedure was employed:

Each sample was placed into a preweighed cell and evacuated. The sample was slowly heated to 425° under vacuum and held at 425° for 18 hrs. After exposing the sample to 375 mm $O_2$ for 30 minutes to burn off any organic material, the sample was evacuated at 425° until the pressure reached $3.7 \times 10^{-5}$ mm Hg ($4.9 \times 10^{-3}$ Pa). At this point, the sample was weighed. The sample was then exposed to 38 mm methanol vapor for 20 hrs, and then weighed again to determine the amount of methanol that had been sorbed. The methanol sorbed per 100 g zeolite could then be calculated. Subtraction of 0.37 g MeOH/100 g zeolite absorbed on the external surface of the zeolite yielded the sorption values indicated in Table IV, below. Quantities of n-propanol sorbed were determined in a similar manner. Table IV lists the amount of methanol and n-propanol sorbed for each of the rho zeolites and the GSI calculated from these measurements. Despite the large increase in selectivity to DMA with increasing calcination temperature, GSI values remain low and essentially constant. This higher selectivity to DMA, at essentially constant GSI, could arise from non-geometric factors induced or enhanced by calcination at progressively higher temperatures, or from geometric factors present at reaction conditions but not at the conditions at which GSI measurements are made, or from a combination of these effects.

TABLE IV

Effect of Calcination Temperature
Upon Geometric Selectivity Indices (GSI)
of Selected Samples of Zeolite H—Rho

| Example | Calcination Temp. (°C.) | Time (hr) | Sorption (g/100 g zeolite) MeOH | n-PrOH | GSI |
|---|---|---|---|---|---|
| 12 | 450 | 65 | 24.7 | 20.6 | 1.2 |
| 13 | 500 | 16 | 20.2 | 13.4 | 1.5 |
| 14 | 625 | 2 | 18.6 | 15.4 | 1.2 |

TABLE IV-continued

Effect of Calcination Temperature
Upon Geometric Selectivity Indices (GSI)
of Selected Samples of Zeolite H—Rho

| Example | Calcination Temp. (°C.) | Time (hr) | Sorption (g/100 g zeolite) MeOH | n-PrOH | GSI |
|---|---|---|---|---|---|
| 15 | 725 | 2 | 20.2 | 16.6 | 1.2 |

EXAMPLE 12

For this example, zeolite H-rho was prepared by a modification of the general procedure described in Robson, U.S. Pat. No. 3,904,738. Three separate samples of Na,Cs-rho were prepared by combining 100 mL 4M $Na_2AlO_2OH$, 16 g NaOH and 27.7 mL 50% CsOH with 357 mL colloidal $SiO_2$ (Ludox ® LS-30) in a 500 mL polypropylene bottle. The resulting mixture was permitted to stand at 25° for 6 days, and then heated on a steam bath for 3 days at 92°-98°. The resulting products were then filtered, dried, and contacted with 23% $NH_4NO_3$ at 90° for 65 hours. An X-ray diffraction pattern disclosed the presence of zeolite $NH_4$-rho and a trace of a chabazite-like impurity. Each of the samples was heated under deep-bed conditions at 400° in air for 2 days. Two of the three samples were combined and contacted with 20% $NH_4NO_3$ at 100° for 2 days. After filtering, washing, and drying, the sample was calcined again under deep-bed conditions at 450° for 65 hrs, cooled, and the resulting zeolite H-rho evaluated as a catalyst substantially according to the procedure described in Example 1, above. The results are set forth in Table V, below.

EXAMPLE 13

A mixture of 200 mL 4M $Na_2AlO_2OH$, 56 mL 50% CsOH, and 26 g NaOH was added to 720 mL of colloidal silica (Ludox ® LS-30) in a polytetrafluoroethylene (Teflon ®) bottle. The resulting preparation was allowed to stand for 7 days at 25° and then for 13 days at 90°. A portion of the resulting zeolite Na,Cs-rho was contacted twice for 16 hrs with a 20% $NH_4NO_3$ solution at 80° to produce zeolite $NH_4$-rho. Zeolite H-rho was prepared by heating the zeolite $NH_4$-rho under deep-bed conditions in air at 250° for 1 hr and then at 500° for 16 hrs. 2 g of the resulting catalyst was evaluated substantially according to the procedure of Example 1. The results of this experiment are set forth in Table V.

EXAMPLES 14 and 15

200 mL 4M Na$_2$AlO$_2$OH, 56 mL 50% CsOH, and 26 g NaOH were added to 720 mL colloidal silica (Ludox® LS-30) in a polytetrafluoroethylene bottle, and permitted to stand for 12 days at 25°. The resulting mixture was then heated for 7 days at 90°, then contacted twice with 20% NH$_4$NO$_3$ at 80°, for about 18 hrs each time, to produce zeolite NH$_4$-rho. This material was then calcined under deep-bed conditions in air at 465° for 16 hrs, followed by 30 minutes at 600°. The resulting preparation was divided into two samples. A first sample, employed in Example 14, was heated for an additional two hours at 625°. The other sample, evaluated in Example 15, was heated for two hours at 725°. In separate experiments, 2 g of each sample were evaluated in a research reactor substantially as described in Example 1. The results of Examples 14 and 15 are set forth in Table V, below.

EXAMPLE 16

Zeolite Na,Cs-rho was prepared according to the following procedure. A mixture of 800 mL of 4M Na$_2$AlO$_2$OH, 224 mL of 50% CsOH, and 104 g NaOH was added to 2880 mL of colloidal SiO$_2$ (Ludox LS-30 ®) in a Teflon ® bottle and allowed to stand at 25° for 11 days. The mixture was heated at 100° for 9 days. The product (Na,Cs-rho) was washed and dried at 110°. This Na,Cs-rho, after washing and filtering, was contacted four times with a 20% NH$_4$NO$_3$ solution at about 90° C. with filtering between each exchange, to produce NH$_4$-rho.

Zeolite H-rho was prepared by heating 5 g of NH$_4$-rho for 1 hr under deep-bed conditions in air at 800°. After cooling, the sample was pressed into a wafer, crushed, granulated and screened.

In an experiment substantially similar to that described in Example 1, methanol and ammonia were passed over a catalyst consisting of 2 g of this preparation of zeolite H-rho, in the form of a 20–40 mesh powder. The conditions employed and results obtained are shown in Table V.

EXAMPLE 17

Zeolite H-rho was prepared by heating 4 g of the powdered zeolite NH$_4$-rho prepared in Example 16 for two weeks under deep-bed conditions in air at 550°. The weight loss during this thermal treatment was 19.5%. The product was zeolite H-rho.

In a procedure substantially the same as that described in Example 1, methanol and ammonia were passed over a catalyst consisting of 2 g of the zeolite H-rho. The conditions employed and results obtained are shown in Table V.

EXAMPLE 18

Zeolite H-rho was prepared as follows. A mixture of 200 mL 4M Na$_2$AlO$_2$OH, 32 g NaOH, and 56 mL 50% CsOH was added to 720 mL of colloidal silica (Ludox® LS-30) and allowed to stand at about 23° for 6 days. This mixture was heated to 100° for 6 days. The resulting product (Na,Cs-rho) was filtered, washed with distilled water, and dried. This procedure was repeated and the dried products of both batches combined. A 50 g sample of the combined Na,Cs-rho product was contacted with 50 mL of a 10% NH$_4$NO$_3$ solution three times at 90° for 1 hr each. After thorough washing with distilled water, the sample (NH$_4$-rho) was dried at 110°. A portion of the dried NH$_4$-rho was then calcined under deep-bed conditions by raising the temperature 50° per hr to 550° and then heating the sample at 550° for 10 hrs to give H-rho. The results of the evaluation of this material, which was conducted substantially as described in Example 1, are set forth in Table V.

EXAMPLE 19

Zeolite NH$_4$-rho was prepared substantially as described in Example 16.

Zeolite H-rho was prepared by slowly heating 250 g of the zeolite NH$_4$-rho under deep-bed conditions, in a slow stream of air, from room temperature to 550° in 30 minutes. The temperature was then held at 550° for 3 hrs. The sample was then allowed to cool to 100°, transferred to a tared jar, sealed, allowed to cool to about 23° and then weighed. The weight of the calcined sample was 223 g, corresponding to a weight loss of about 9%. Chemical analysis showed that the sample contained, by weight, 3.3% Cs, 9% Al, and 160 ppm Na. The product was zeolite H-rho.

NH$_4$-rho was prepared by contacting 150 g of the resulting product H-rho with 1500 mL of a 10% NH$_4$NO$_3$ solution at 90° three times for 1 hour each. After thorough washing with distilled water, the sample was dried at 110°. The resulting NH$_4$-rho was calcined by raising the temperature 50° per hr to a final temperature of 700° and heating the sample at 700° for 10 hrs to give H-rho. This material was evaluated substantially as described in Example 1, and the results are set forth in Table V, below.

EXAMPLES 20–23

The results of Examples 20–23 demonstrate that shallow-bed calcination techniques provide H-rho zeolite catalysts with exceptionally high selectivities to DMA.

Portions of the sample of NH$_4$-rho prepared in Examples 3–11 were converted to H-rho by a shallow-bed calcination technique. A sample consisting of 5.0 g of NH$_4$-rho was spread out in an Al$_2$O$_3$ boat, passed into the hot zone of a belt furnace at 0.64 cm/minute, and held at 400° for 27 hrs under a N$_2$ flow of 20 L/min. An infra-red spectrum indicated, from the absence of an absorption band at 1400 cm$^{-1}$, that substantially all NH$_4$+ ions had decomposed, giving H-rho containing essentially no NH$_4$+. A series of samples were prepared by this shallow-bed calcination technique at different temperatures under the conditions indicated in Table VI. Each sample was evaluated substantially according to the procedure of Example 1. Results are set forth in Table VI, below.

TABLE VI

Effect of Deep-Bed Calcinations Upon Selectivity of Zeolite H—rho for Methylamines

| Example | Calcination T (°C.) | Calcination Time (hr) | Reaction T (°C.) | Feed Flow (mL/hr) | MeOH—MA Conv. (%) | MeOH—DME Conv. (%) | Selectivity (%) MMA | DMA | TMA |
|---|---|---|---|---|---|---|---|---|---|
| 12 | 450 | 65 | 300 | 4 | 95 | 1 | 19 | 31 | 50 |
| 13 | 500 | 16 | 300 | 8 | 88 | 1 | 20 | 39 | 41 |
| 14 | 625 | 2 | 300 | 8 | 88 | 1 | 22 | 47 | 31 |
| 15 | 725 | 2 | 300 | 8 | 90 | 2 | 24 | 52 | 24 |
| 16 | 800 | 1 | 300 | 4 | 64 | 25 | 17 | 73 | 10 |
| 17 | 550 | 356 | 300 | 8 | 91 | 3 | 17 | 54 | 28 |
| 18 | 550 | 10 | 300 | 8 | 87.4 | 2.6 | 13 | 50 | 37 |
| 19 | 770 | 10 | 300 | 6 | 74 | 11 | 21 | 64 | 16 |

TABLE VI

Effect of Shallow-Bed Calcinations Upon Selectivity of Zeolite H—rho for Methylamines

| Example | Calcination T (°C.) | Calcination Time (hr) | Reaction T (°C.) | Feed Flow (mL/hr) | MeOH—MA Conv. (%) | MeOH—DME Conv. (%) | Selectivity (%) MMA | DMA | TMA |
|---|---|---|---|---|---|---|---|---|---|
| 20 | 400 | 27 | 328 | 3 | 88.3 | 4.7 | 14 | 54 | 32 |
| 21 | 500 | 16 | 325 | 3 | 84.7 | 4.3 | 16 | 60 | 24 |
| 22 | 600 | 4 | 300 | 2 | 83 | 7 | 16 | 76 | 8 |
| 23 | 700 | 4 | 325 | 2 | 87.3 | 6.7 | 15 | 74 | 11 |

EXAMPLES 24–27

Examples 24–27 illustrate the enhancement of dimethylamine selectivity provided when zeolite H-rho is treated with NaOH, further exchanged with $NH_4NO_3$ solution, and then calcined.

EXAMPLES 24 and 25

Zeolite H-rho was prepared by heating a portion of the $NH_4$-rho prepared in Examples 3–11 at 545° in air for 6 hrs. Analysis indicated that the product zeolite H-rho had the composition $H_{10.0}Cs_{0.8}Al_{10.8}Si_{37.2}O_{96} \cdot 54 H_2O$. A portion of this material was reserved for evaluation as Example 24.

Another portion of the zeolite H-rho was slurred at 25° for 14 hours with 500 mL of 1N NaOH solution to prepare Na-rho. This slurry was filtered, washed thoroughly, and exchanged twice with 500 mL of a 20% $NH_4NO_3$ solution. After filtration, washing and drying, the resulting material was calcined for 6 hours in air at 550°. This two stage process (slurrying with 1N NaOH, recovery and reslurrying twice with 20% $NH_4NO_3$) was then repeated. After a final calcination at 550° for 6 hours, the product was analyzed, indicating the following composition:

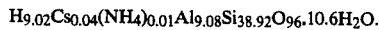

$H_{9.02}Cs_{0.04}(NH_4)_{0.01}Al_{9.08}Si_{38.92}O_{96} \cdot 10.6H_2O$.

In a procedure substantially the same as that described in Example 1, methanol and ammonia were passed over a catalyst consisting of 2 g of the zeolite H-rho of Example 24 and 2 g of the zeolite H-rho of Example 25. The conditions employed and results obtained are shown in Table VII.

EXAMPLES 26 and 27

Zeolite H-rho was prepared as follows. A mixture of 400 mL 4N $Na_2AlO_2OH$, 112 mL 50% CsOH, and 64 g NaOH was added to 1440 mL of colloidal silica (Ludox® LS-30) in a polytetrafluoroethylene container, and allowed to stand 6 days at 25°. The resulting material was then heated at 100° until crystalline, as determined by powder X-ray diffraction. The resulting product was filtered, washed and dried at 110°. The foregoing procedure was substantially repeated for a second batch, which was combined with the product of the first batch. 750 g of the combined products were contacted three times, for one hour each time, with 7500 mL of a 10% $NH_4NO_3$ solution at 90° to produce zeolite $NH_4$-rho. Zeolite H-rho was prepared by calcining this material under deep-bed conditions, in air, by raising the calcination temperature 60° per hour to 550°, and then holding the sample at 550° for 10 hours. A sample of this material was reserved for evaluation as Example 26.

300 g of the zeolite H-rho prepared above were stirred in 750 mL 1N NaOH for 24 hours. The treated zeolite was then filtered, washed with distilled water and methanol, and then dried at 110°. The dried zeolite was then slurried in 10% $NH_4NO_3$ three times, for one hour each time, at 90°. After thorough washing again with water and methanol, the sample was again dried at 110°. The resulting material was then calcined in air by raising the temperature 60° per hour to a final temperature of 550° and heating the material at 550° for 10 hours. The entire procedure described above was then repeated. The resulting material was given the designation "NaOH-treated H-rho".

Using a procedure substantially similar to that described in Example 1, methanol and ammonia were contacted with 2 g of the H-rho prepared as Example 26 and 2 g of the NaOH-treated H-rho prepared as Example 27. The results are set forth in Table VII, below.

The lower DMA selectivities of Examples 26 and 27 are believed to result from the presence of amorphous contaminants.

TABLE VII

Effect of NaOH Precalcination Treatment
Upon Dimethylamine Selectivity of Zeolite H—Rho

| | Reaction | | MeOH | MeOH— | Selectivity (%) | | |
|---|---|---|---|---|---|---|---|
| Example | Temp. (°C.) | Flow (mL/hr) | Conv. (%) | MA Conv. (%) | MMA | DMA | TMA |
| 24 | 300 | 12 | 87 | 86 | 21 | 57 | 22 |
| 25 | 300 | 6 | 89 | 88 | 20 | 73 | 7 |
| 26 | 300 | 4 | 93 | 91 | 11 | 35 | 53 |
| 27 | 300 | 4 | 94 | 91 | 15 | 55 | 29 |

EXAMPLES 28 and 29

Examples 28 and 29 demonstrate the selectivity to dimethylamine of zeolite H-rho and zeolite Ca-rho.

To prepare cation-exchanged samples of zeolite H-rho, a mixture of 270 mL 4M $Na_2AlO_2OH$, 74.8 mL 50% CsOH, and 43.2 g NaOH was added to 964 mL colloidal silica (Ludox® LS-30) in a polytetrafluoroethylene bottle and allowed to stand for 6 days at 25°, followed by 3 days at 100°. The resulting Na,Cs-rho was then exchanged twice (48 hours and 96 hours) with 20% $NH_4NO_3$ at 90° to produce $NH_4$-rho. Zeolite H-rho was prepared from the resulting $NH_4$-rho by heating in air at 450° for 16 hours. Some of this H-rho was evaluated as Example 28.

To prepare Ca-rho for evaluation as Example 29, a portion of the H-rho prepared above was slurried with 0.6 g of $Ca(OH)_2$ in 200 mL $H_2O$ at 25° for 6 days. The resulting product, designated Ca-rho, exhibited a Ca/Al ratio of 1.23. A non-zeolite Ca-containing phase may also have been present.

Each of the samples prepared above was evaluated by dimethylamine selectivity and catalytic performance substantially according to the procedure of Example 1. The results and conditions of Examples 28 and 29 are set forth in Table VIII, below.

time, with 5 L of a 10% $NH_4NO_3$ solution at 90° to produce zeolite $NH_4$-rho.

Some of the zeolite $NH_4$-rho prepared above was pressed into a wafer at 20,000 psi, crushed, and sieved to provide a −20/+40 ASTM Std. Sieve No. (425 μm-850 μm) powder. 10 g of this sieved powder was placed in a quartz tube in a vertically mounted tube furnace under a stream of nitrogen flowing at a rate of about 77 $cm^3$/min and calcined by raising the temperature 60° per hour to 550° and then holding the temperature at 550° for 10 hours. The resulting material was cooled under flowing nitrogen and unloaded in an inert atmosphere glove box under dry nitrogen; the resulting product was designated "dehydrated zeolite H-rho".

One gram of "dehydrated zeolite H-rho" was placed in the stainless-steel U-tube reactor described in Example 1 in the glovebox to prevent exposure to room humidity. The sample was evaluated as a catalyst substantially as described in Example 1. The reactant feed flow was 8 mL/hr. The conditions employed and the results obtained are shown in Table IX.

Five grams of "dehydrated zeolite H-rho" were placed in a desiccator with a saturated solution of $NH_4Cl$ for several days to produce "hydrated zeolite H-rho".

One gram of "hydrated zeolite H-rho" was evaluated

TABLE VIII

Effects of Cation Exchange Upon
Selectivity of Zeolite H—rho

| Example | Zeolite Catalyst | Temp. (°C.) | Feed Flow (mL/hr) | MeOH Conv. (%) | MeOH— MA Conv. (%) | Selectivity (%) | | |
|---|---|---|---|---|---|---|---|---|
| | | | | | | MMA | DMA | TMA |
| 28 | H—rho | 300 | 5 | 91 | 89 | 12 | 45 | 43 |
| 29 | Ca—rho | 350 | 2 | 94 | 89 | 16 | 51 | 33 |

EXAMPLES 30–31

The results of Examples 30–31 demonstrate the increased DMA selectivity and increased activity provided by zeolite rho in a partially- or totally-hydrated state.

EXAMPLE 30

Zeolite H-rho was prepared as follows. A mixture of 400 mL 4M $Na_2AlO_2OH$, 112 mL 50% CsOH, and 64 g NaOH was added to 1440 mL of colloidal silica (Ludox® LS-30) in a polytetrafluoroethylene (Teflon®) container, and allowed to stand 6 days at 25°. The resulting material was then heated at 90° C. for 3 days. The resulting product was filtered, washed and dried. The foregoing procedure was substantially repeated for a second batch, which was combined with the product of the first batch. The product contained primarily zeolite rho but also a substantial amount of pollucite, as determined by X-ray diffraction. 500 g of the combined products were contacted three times, for one hour each as a catalyst substantially as described in Example 1. The reactant feed flow was 8 mL/hr. The conditions employed and the results obtained are shown in Table IX.

EXAMPLE 31

Zeolite H-rho was prepared as follows. A mixture of 200 mL 4M $Na_2AlO_2OH$, 56 mL 50% CsOH, and 26 g NaOH was added to 720 mL of colloidal silica (Ludox® LS-30) in a polytetrafluoroethylene container and allowed to stand 6 days at 25°. The resulting mixture was heated at 95° for five days. The resulting material was washed and contacted three times, for one hour each time, with a 10% $NH_4NO_3$ solution to produce zeolite $NH_4$-rho.

Portions of this zeolite $NH_4$-rho were converted to zeolite H-rho by the shallow-bed calcination technique described in Examples 20-23 and the product was pelletized, crushed, and sieved to −20/+40 mesh as described in Example 1.

A two gram sample of this zeolite H-rho was exposed to the open atmosphere for 7½ months to produce "hydrated zeolite H-rho". This sample was evaluated as a catalyst substantially as described in Example 1. The conditions employed and the results obtained are shown in Table IX.

A second two gram portion of this zeolite H-rho was placed in the reactor and was dried in flowing $N_2$ at 200° for ½ hour and at 300° for 45 minutes prior to admitting the reactants to produce "dehydrated zeolite H-rho". This sample was evaluated as a catalyst substantially as described in Example 1. The conditions employed and the results obtained are shown in Table IX.

TABLE IX

Effects of Hydration Upon Selectivity and Activity of Zeolite H—Rho

| Ex. | State of H—rho Catalyst | Reaction Temp. (°C.) | MeOH Conv. (%) | MeOH— MA Conv. (%) | Activity MeOH Space Time (g/g/h)* | Selectivity (%) | | |
|---|---|---|---|---|---|---|---|---|
| | | | | | | MMA | DMA | TMA |
| 30 | Dehydrated | 375 | 90 | 82 | 1.5 | 6 | 29 | 66 |
| | Hydrated | 375 | 91 | 81 | 1.1** | 8 | 41 | 52 |
| 31 | Dehydrated | 300 | 90 | 84 | 0.75 | 17 | 48 | 35 |
| | Hydrated | 325 | 95 | 90 | 0.46 | 14 | 80 | 6 |

*Methanol space time with 90% MeOH conversion and 325° reaction temperature.
**Hydrated space times are calculated on the basis of a dry catalyst.

COMPARATIVE EXPERIMENTS A-E

Comparative Experiments A-E demonstrate that certain zeolites having ports bounded by 8 aluminosilicate tetrahedra, for example, erionite, and zeolites having ports bounded by 10 or 12 aluminosilicate tetrahedra, for example, ferrierite, silicalite, and zeolite Y, display little or no selectivity to dimethylamine when compared to the values attained at equilibrium for the uncatalyzed reaction of methanol and ammonia. Similar results are obtained when an alumina-silica catalyst (91% $Al_2O_3$, 6.5% $SiO_2$) is employed. Comparison of the results of Comparative Experments, A, B, C and E with examples of the invention conducted at similar flow rates suggest that comparable conversions can be obtained with acidic zeolite rho at temperatures 100° below those employed in the Comparative Experiments.

COMPARATIVE EXPERIMENT A

Zeolite H-ferrierite was prepared by heating a sample of ferrierite (Zeolon ®700, Norton Company) to 500° in flowing $N_2$ for 10 hours and then contacting the resulting sample three times, for one hour each time, with a 10% $NH_4NO_3$ solution at 80°. The resulting material was dried and heated by increasing the temperature 50° per hour to 500°, and then held at 500° for ten hours. The resulting sample of H-ferrierite was then cooled and evaluated for dimethylamine selectivity by a procedure substantially similar to that described in Example 1. The conditions employed and the results obtained are set forth in Table X, below.

COMPARATIVE EXPERIMENT B

Zeolite H-erionite was prepared from a sampler 1 of zeolite $NH_4$-erionite (Linde E-10) by a procedure substantially similar to that described for preparation of H-ferrierite in Comparative Experiment A. The resulting material was evaluated for dimethylamine selectivity substantially according to the procedure of Example 1. The results obtained are set forth in Table X, below.

COMPARATIVE EXPERIMENT C

Methanol and ammonia were passed over a catalyst consisting of 2 g of zeolite H-silicalite (S-115, Union Carbide Corporation) substantially as described in Example 1. The conditions and results are displayed in Table X. This material sorbed 12.5 g methanol and 12.5 g n-propanol per 100 g catalyst, providing a GSI of 1.

COMPARATIVE EXPERIMENT D 100 g of zeolite $NH_4$-Y (Linde LZY-82) was calcined in air by heating in 50° stepwise increments to 540°, and then held at 540° for about 10 hours. The resulting product, zeolite H-Y, was evaluated for dimethylamine selectivity by a procedure substantially similar to that described in Example 1. The conditions and results are set forth in Table X.

COMPARATIVE EXPERIMENT E

In a procedure substantially similar to that described in Example 1, methanol and ammonia were passed over a catalyst consisting of 2 g of silica-alumina (91% $Al_2O_3$, 6.5% $SiO_2$; Harshaw Chemical Co., Al-1602T). The conditions and results are displayed in Table X, below.

TABLE X

Methylamine Selectivities of Erionite, 10- and 12-Ring Zeolites, and Silica-Alumina Catalysts

| Comparative Experiment | Catalyst | T (°) | Feed Flow (mL/hr) | MeOH Conv. (%) | MeOH— MA Conv. (%) | Selectivity (%) | | |
|---|---|---|---|---|---|---|---|---|
| | | | | | | MMA | DMA | TMA |
| A | H—ferrierite | 400 | 0.5 | 94 | 90 | 13 | 28 | 59 |
| B | H—erionite | 400 | 2 | 98 | 98 | 18 | 31 | 51 |
| C | H—silicalite | 400 | 4 | 97 | 92 | 9 | 22 | 69 |
| D | H—Y LZY-82 | 300 | 4 | 94 | 70 | 1 | 4 | 95 |
| E | Harshaw Al 1602 | 400 | 6 | 92 | 80 | 11 | 14 | 75 |

TABLE X-continued

Methylamine Selectivities of Erionite,
10- and 12-Ring Zeolites, and Silica-Alumina Catalysts

| Comparative Experiment | Catalyst | T (°) | Feed Flow (mL/hr) | MeOH Conv. (%) | MeOH—MA Conv. (%) | Selectivity (%) | | |
| --- | --- | --- | --- | --- | --- | --- | --- | --- |
| | | | | | | MMA | DMA | TMA |
| | Equilibrium | 400 | | | | 10 | 22 | 68 |

What is claimed is:

1. A process for producing dimethylamine comprising reacting methanol and/or dimethylether and ammonia, in amounts sufficient to provide a carbon/nitrogen (C/N) ratio from about 0.2 to about 1.5, at a temperature from about 250° C. to about 450° C., in the presence of a catalytic amount of an acidic zeolite rho, provided that the zeolite rho has not been modified by treatment with one or more compounds containing at least one element selected from the group consisting of silicon, aluminum, phosphorus, and boron, to deposit thereon at least 0.05 weight percent of the element.

2. A process according to claim 1, conducted at a pressure from 7 to 7000 kPa and at a reactant feed rate sufficient to provide a methanol/DME space time of 0.01 to 80 hours.

3. A process according to claim 2, wherein the temperature is from 300° C. to 400° C.

4. A process according to claim 3, wherein the pressure is from 70 to 3000 kPa, and the methanol/DME space time is from 0.10 to 1.5 hours.

5. A process according to claim 4, wherein the C/N ratio is from about 0.5 to about 1.2.

6. A process according to claim 1, wherein the zeolite catalyst is zeolite H-rho.

7. A process according to claim 2, wherein the zeolite catalyst is zeolite H-rho.

8. A process according to claim 3, wherein the zeolite catalyst is zeolite H-rho.

9. A process according to claim 4, wherein the zeolite catalyst is zeolite H-rho.

10. A process according to claim 5, wherein the zeolite catalyst is zeolite H-rho.

11. A process according to claim 1, wherein the zeolite catalyst is hydrated acidic zeolite rho.

12. A process according to claim 2, wherein the zeolite catalyst is hydrated acidic zeolite rho.

13. A process according to claim 3, wherein the zeolite catalyst is hydrated acidic zeolite rho.

14. A process according to claim 4, wherein the zeolite catalyst is hydrated acidic zeolite rho.

15. A process according to claim 5, wherein the zeolite catalyst is hydrated acidic zeolite rho.

16. A process according to claim 6, wherein the zeolite catalyst is hydrated zeolite H-rho.

17. A process according to claim 7, wherein the zeolite catalyst is hydrated zeolite H-rho.

18. A process according to claim 8, wherein the zeolite catalyst is hydrated zeolite H-rho.

19. A process according to claim 9, wherein the zeolite catalyst is hydrated zeolite H-rho.

20. A process according to claim 10, wherein the zeolite catalyst is hydrated zeolite H-rho.

21. A process according to claim 6, wherein the zeolite catalyst is zeolite H-rho prepared by calcination of $NH_4$-rho at a temperature from 400° C. to 800° C.

22. A process according to claim 21, wherein the zeolite catalyst is zeolite H-rho prepared by calcination of $NH_4$-rho under shallow-bed conditions at a temperature from 600° C. to 750° C.

23. A process according to claim 21, wherein the zeolite catalyst is zeolite H-rho prepared by calcination of $NH_4$-rho under deep-bed conditions at a temperature from 500° C. to 800° C.

24. A process according to claim 23, wherein the zeolite catalyst is zeolite H-rho prepared by calcination of $NH_4$-rho under deep-bed conditions at a temperature from 500° 1 C. to 650° C.

25. A process according to claim 10, wherein the zeolite catalyst is zeolite H-rho prepared by treating zeolite H-rho with 0.5 to 5N NaOH, contacting the resulting product with aqueous $NH_4^+$, and calcining at a temperature from 500° C. to 650° C.

26. A process according to claim 5, wherein the zeolite catalyst is zeolite Ca-rho.

* * * * *